(12) United States Patent
Brandt et al.

(10) Patent No.: US 11,918,670 B2
(45) Date of Patent: Mar. 5, 2024

(54) MIXTURE COMPOSITION COMPRISING GLYCOLIPIDS AND TRIETHYL CITRATE

(71) Applicants: Evonik Operations GmbH, Essen (DE); Evonik Dr. Straetmans GmbH, Hamburg (DE)

(72) Inventors: Kathrin Daniela Brandt, Duesseldorf (DE); Stefan Julian Liebig, Duesseldorf (DE); Hans Henning Wenk, Muelheim an der Ruhr (DE); Manuela Salmina-Petersen, Hamburg (DE); Christoph Tölle, Duisburg (DE); Alina Muss, Essen (DE)

(73) Assignees: Evonik Operations GmbH, Essen (DE); Evonik Dr. Straelmans GmbH, Hamburg (DE)

( * ) Notice: Subject to any disclaimer, the term of this patent is extended or adjusted under 35 U.S.C. 154(b) by 0 days.

(21) Appl. No.: 17/905,835

(22) PCT Filed: Mar. 8, 2021

(86) PCT No.: PCT/EP2021/055712
§ 371 (c)(1),
(2) Date: Sep. 8, 2022

(87) PCT Pub. No.: WO2021/180612
PCT Pub. Date: Sep. 16, 2021

(65) Prior Publication Data
US 2023/0121094 A1    Apr. 20, 2023

(30) Foreign Application Priority Data

Mar. 11, 2020    (EP) .................................... 20162304

(51) Int. Cl.
*C11D 3/22*    (2006.01)
*A61K 8/04*    (2006.01)
(Continued)

(52) U.S. Cl.
CPC ................ *A61K 8/37* (2013.01); *A61K 8/046* (2013.01); *A61K 8/602* (2013.01); *A61Q 19/10* (2013.01)

(58) Field of Classification Search
CPC ..... C11D 1/662; C11D 3/2075; C11D 3/2086; C11D 3/22; A61K 8/04; A61K 8/046;
(Continued)

(56) References Cited

U.S. PATENT DOCUMENTS

| 8,911,982 B2 | 12/2014 | Schaffer et al. |
| 9,068,211 B2 | 6/2015 | Schaffer et al. |

(Continued)

FOREIGN PATENT DOCUMENTS

| DE | 102012201360 | 8/2013 |
| EP | 2501813 | 9/2012 |

(Continued)

OTHER PUBLICATIONS

Extended European Search Report dated Sep. 10, 2020 in European Patent Application No. 20162304.8, 6 pages.
(Continued)

*Primary Examiner* — Brian P Mruk
(74) *Attorney, Agent, or Firm* — Grüneberg and Myers PLLC

(57) ABSTRACT

A composition contains glycolipids and triethyl citrate (TEC). The TEC can assist in stabilizing a foam of a corresponding aqueous composition. A method can be used for preparing a corresponding formulation, preferably a cosmetical or pharmaceutical formulation, by providing the composition and diluting the composition. The pH of the composition may be adjusted during the dilution by adding an organic or inorganic base.

19 Claims, 5 Drawing Sheets

(51) Int. Cl.
*A61K 8/365* (2006.01)
*A61K 8/37* (2006.01)
*A61K 8/60* (2006.01)
*A61Q 19/10* (2006.01)

(58) Field of Classification Search
CPC . A61K 8/365; A61K 8/37; A61K 8/60; A61K 8/602; A61Q 19/10
See application file for complete search history.

(56) References Cited

U.S. PATENT DOCUMENTS

| | | | |
|---|---|---|---|
| 9,085,787 | B2 | 7/2015 | Schaffer et al. |
| 9,102,968 | B2 | 8/2015 | Schaffer et al. |
| 9,157,108 | B2 | 10/2015 | Schaffer et al. |
| 9,243,212 | B2 | 1/2016 | Kuppert et al. |
| 9,271,908 | B2 | 3/2016 | Allef et al. |
| 9,351,485 | B2 | 5/2016 | Giessler-Blank et al. |
| 9,434,755 | B2 | 9/2016 | Schilling et al. |
| 9,580,720 | B2 | 2/2017 | Schaffer et al. |
| 10,174,353 | B2 | 1/2019 | Thum et al. |
| 10,292,924 | B2 | 5/2019 | Schilling et al. |
| 10,544,384 | B2 | 1/2020 | Scheuermann et al. |
| 10,604,722 | B2 | 3/2020 | Schilling et al. |
| 10,676,495 | B2 | 6/2020 | Lu et al. |
| 10,941,173 | B2 | 3/2021 | Lu et al. |
| 10,988,713 | B2 | 4/2021 | Schilling et al. |
| 11,236,372 | B2 | 2/2022 | Wessel et al. |
| 11,254,896 | B2 | 2/2022 | Kuppert et al. |
| 11,464,717 | B2 | 10/2022 | Wenk et al. |
| 2012/0220464 | A1 | 8/2012 | Giessler-Blank et al. |
| 2013/0035403 | A1 | 2/2013 | Schaffer et al. |
| 2014/0148588 | A1 | 5/2014 | Schilling et al. |
| 2014/0296125 | A1* | 10/2014 | Kuppert .................. C11D 1/74 510/356 |
| 2014/0296168 | A1 | 10/2014 | Schilling et al. |
| 2014/0349902 | A1 | 11/2014 | Allef et al. |
| 2015/0056658 | A1 | 2/2015 | Schaffer et al. |
| 2015/0056659 | A1 | 2/2015 | Schaffer et al. |
| 2015/0056660 | A1 | 2/2015 | Schaffer et al. |
| 2015/0056661 | A1 | 2/2015 | Schaffer et al. |
| 2015/0247151 | A1 | 9/2015 | Schaffer et al. |
| 2016/0045424 | A1 | 2/2016 | Schwab et al. |
| 2016/0249604 | A1 | 9/2016 | Giessler-Blank et al. |
| 2017/0094968 | A1 | 4/2017 | Sieverding |
| 2017/0096695 | A1 | 4/2017 | Thum et al. |
| 2017/0306264 | A1 | 10/2017 | Peggau et al. |
| 2017/0335238 | A1 | 11/2017 | Schilling et al. |
| 2018/0016525 | A1 | 1/2018 | Scheuermann et al. |
| 2018/0023040 | A1 | 1/2018 | Schilling et al. |
| 2018/0066297 | A1 | 3/2018 | Haas et al. |
| 2019/0031977 | A1 | 1/2019 | Kuppert et al. |
| 2019/0040095 | A1 | 2/2019 | Lu et al. |
| 2019/0233856 | A1 | 8/2019 | Thum et al. |
| 2019/0256542 | A1 | 8/2019 | Lu et al. |
| 2019/0269158 | A1 | 9/2019 | Schilling et al. |
| 2019/0271020 | A1 | 9/2019 | Thum et al. |
| 2019/0307657 | A1 | 10/2019 | Wenk et al. |
| 2020/0199492 | A1 | 6/2020 | Xue et al. |
| 2020/0214959 | A1 | 7/2020 | Lu et al. |
| 2020/0407761 | A1 | 12/2020 | Wessel et al. |
| 2021/0337835 | A1 | 11/2021 | Schilling et al. |
| 2021/0371773 | A1 | 12/2021 | Brandt et al. |
| 2022/0183958 | A1 | 6/2022 | Kleinen et al. |
| 2022/0186048 | A1 | 6/2022 | Reuter et al. |
| 2022/0186075 | A1 | 6/2022 | Reuter et al. |

FOREIGN PATENT DOCUMENTS

| | | | |
|---|---|---|---|
| EP | 2786742 | 10/2014 | |
| WO | 01/10391 | 2/2001 | |
| WO | 2011/061032 | 5/2011 | |
| WO | 2019/154970 | 8/2019 | |
| WO | WO 2019/154970 | * 8/2019 | ........... C07K 14/195 |
| WO | 2021/190993 | 9/2021 | |
| WO | 2022/017844 | 1/2022 | |
| WO | 2022/148758 | 7/2022 | |

OTHER PUBLICATIONS

International Search Report dated Jun. 7, 2021 in International Patent Application No. PCT/EP2021/055712, 4 pages.
Özdemir et al., "Effect of pH on the surface and interfacial behavior of rhamnolipids R1 and R2", Colloids and Surfaces A: Physicochem. Eng. Aspects 234, (2004), pp. 135-143.
Written Opinion dated Jun. 7, 2021 in International Patent Application No. PCT/EP2021/055712, 7 pages.
U.S. Appl. No. 15/151,021, filed May 10, 2016, 2016/0249604, Giessler-Blank et al.
U.S. Appl. No. 15/311,217, filed Nov. 15, 2016, 2017/0094968, Ewald Sieverding.
U.S. Appl. No. 15/509,685, filed Mar. 8, 2017, 2017/0306264, Peggau et al.
U.S. Appl. No. 14/783,142, filed Oct. 8, 2015, 2016/0045424, Schwab et al.
U.S. Appl. No. 15/551,904, filed Aug. 18, 2017, 2018/0066297, Haas et al.
U.S. Appl. No. 16/333,719, filed Mar. 15, 2019, 2019/0271020, Thum et al.
U.S. Appl. No. 16/334,781, filed Mar. 20, 2019, 2019/0233856, Thum et al.
U.S. Appl. No. 16/332,979, filed Mar. 13, 2019, 2019/0269158, Schilling et al.
U.S. Appl. No. 17/369,275, filed Jul. 7, 2021, 2021/0337835, Schilling et al.
U.S. Appl. No. 16/608,791, filed Oct. 25, 2019, 2020/0199492, Xue et al.
U.S. Appl. No. 16/631,248, filed Jan. 15, 2020, 2020/0214959, Lu et al.
U.S. Appl. No. 17/436,104, filed Sep. 3, 2021, 2022/0183958, Kleinen et al.
U.S. Appl. No. 16/963,277, filed Jul. 20, 2020, 2021/0371773, Brandt et al.
U.S. Appl. No. 17/643,630, filed Dec. 10, 2021, 2022/0186075, Reuter et al.
U.S. Appl. No. 17/547,575, filed Dec. 10, 2021, 2022/0186048, Reuter et al.

* cited by examiner

MIXTURE COMPOSITION COMPRISING GLYCOLIPIDS AND TRIETHYL CITRATE

CROSS-REFERENCE TO RELATED APPLICATIONS

This application is the National Stage entry under § 371 of International Application No. PCT/EP2021/055712, filed on Mar. 8, 2021, and which claims the benefit of priority to European Application No, 20162304.8, filed on Mar. 11, 2020. The content of each of these applications is hereby incorporated by reference in its entirety.

BACKGROUND OF THE INVENTION

Field of the Invention

The instant invention relates to a composition comprising Glycolipids and Triethyl Citrate (TEC).

Description of Related Art

Rhamnolipids are anionic surfactants with unique properties like cleansing characteristics, biodegradability and strong foaming ability. Commercial availability of rhamnolipids increased over the past years across different application areas. In cosmetic applications, the foaming ability of rhamnolipids is of special interest. Fast flash foaming and high foam volumes are indications to the consumers that the product is an efficacious quality product. Anyhow, the foaming behaviour of rhamnolipids is depending on the pH value of the formulation. Ozdemir et al. describe the effect of pH on the surface and interfacial behaviour (Colloids Surf. A 2004, 234, 135-143). One disadvantage of the behaviour described in the state of the art consists in the fact, that a pH as high as pH 7 is required for fast foam creation. At lower pH the foaming ability is decreased. Cosmetic compositions are typically formulated at a pH below 7 down to values like pH 5. Here the foaming ability of rhamnolipids is strongly decreased.

To overcome this problem additives can be applied. Non-ionic surfactants like fatty acid alkanolamides are available in the market as foam boosters. These substances can contain traces of nitrosamines and are based on tropical oils. WO2001010391A2 describes the use of alkoxylated carboxylic acid esters as foam boosters. The alkoxylation step leads to measurable 1,4-dioxane levels, which is an unwanted by-product for cosmetic applications.

In the cosmetics and personal care sector, triethyl citrate is used as a perfume fixer and as a film for hair sprays and nail polish. It is also used as an active ingredient in deodorants.

Triethyl citrate is used as a food additive (E number E1505) amongst others to stabilize albuminous foams, for example as whipping aid for egg white.

SUMMARY OF THE INVENTION

An object of the present invention was to provide compositions with improved foaming ability of rhamnolipids, especially at cosmetically widely used pH-values, preferably in acidic environment. Surprisingly, it has been found that the mixture composition described below is able to achieve the object addressed by the invention.

One advantage of the mixture compositions according to the invention is their excellent foaming properties.

A further advantage of the mixture compositions according to the invention is their outstanding flash foaming under aqueous conditions.

A further advantage of the mixture compositions according to the invention is their exceptionally high foam volume under aqueous conditions.

A further advantage of the mixture compositions according to the invention is their low viscosity and therefore simple processability in any desired aqueous surface-active system.

A further advantage of the mixture compositions according to the invention is their good skin and hair cleansing properties.

A further advantage of the mixture compositions according to the invention is their very good solubilizing efficacy for essential oils at low usage levels.

A further advantage of the mixture compositions according to the invention is their mildness and good physiological compatibility, in particular characterized by a high value in the red blood cell (RBC) test.

A further advantage of the mixture compositions according to the invention is their good skin feel during and after washing.

A further advantage of the mixture compositions according to the invention is that they leave behind a smooth and soft skin feel after washing.

A further advantage of the mixture compositions according to the invention is that they can be synthesized free from petrochemical raw materials.

A further advantage of the mixture compositions according to the invention is that they can be synthesized free from critical raw materials such as tropical oils.

A further advantage of the mixture compositions according to the invention is their outstanding microbiological stability.

A further advantage of the mixture compositions according to the invention is that the dependency of foaming ability towards pH is reversed compared to pure glycolipids, especially rhamnolipids.

Compositions are described, comprising
0.2% by weight to 70% by weight, preferably 0.4% by weight to 55% by weight of at least one glycolipid,
0.01% by weight to 14% by weight, preferably 0.02% by weight to 11% by weight, triethyl citrate, and
water,
where the percentages by weight refer to the total composition, characterized in that the weight ratio of all glycolipids to all triethyl citrate comprised in the composition is in the range of from 5:1 to 20:1, preferably from 6:1 to 15:1, particular preferably from 7:1 to 12:1.

DETAILED DESCRIPTION OF THE INVENTION

The "pH" in connection with the present invention is defined as the value which is measured for the relevant composition at 25° C. after stirring for five minutes using a pH electrode calibrated in accordance with ISO 4319 (1977).

The term "preservative" in the context of the present invention is understood to mean an agent which preserves with regard to microbial, particularly bacterial, growth.

In connection with the present invention, the term "aqueous" is understood as meaning a composition which comprises at least 5.0% by weight of water, based on the total composition under consideration.

Unless stated otherwise, all the stated percentages (%) are percentages by mass.

Preferred compositions according to the instant invention comprise a glycolipid selected from the group of rhamnolipids, glucolipids and sophorolipids, in particular rhamnolipids and glucolipids, in most particular rhamnolipids.

The term "rhamnolipid" in the context of the present invention encompasses rhamnolipids, protonated forms thereof and also in particular salts thereof.

The term "rhamnolipid" in the context of the present invention is understood to mean particularly mixtures of compounds of the general formula (I) and salts thereof,

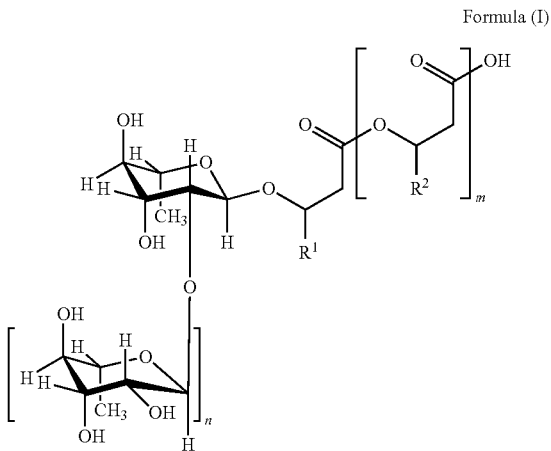

Formula (I)

where
m=2, 1 or 0,
n=1 or 0,
$R^1$ and $R^2$=mutually independently, identical or different, organic radical having 2 to 24, preferably 5 to 13 carbon atoms, in particular optionally branched, optionally substituted, particularly hydroxy-substituted, optionally unsaturated, in particular optionally mono-, bi- or tri-unsaturated alkyl radical, preferably that selected from the group consisting of pentenyl, heptenyl, nonenyl, undecenyl and tridecenyl and $(CH_2)_o$—$CH_3$ where o=1 to 23, preferably 4 to 12.

If n=1, the glycosidic bond between the two rhamnose units is preferably in the α-configuration. The optically active carbon atoms of the fatty acids are preferably present as R-enantiomers (e.g. (R)-3-{(R)-3-[2-O-(α-L-rhamnopyranosyl)-α-L-rhamnopyranosyl]oxydecanoyl}oxydecanoate).

The term "di-rhamnolipid" in the context of the present invention is understood to mean compounds of the general formula (I) or salts thereof, where n=1.

The term "mono-rhamnolipid" in the context of the present invention is understood to mean compounds of the general formula (I) or salts thereof, where n=0.

Distinct rhamnolipids are abbreviated according to the following nomenclature:

"diRL-CXCY" is understood to mean di-rhamnolipids of the general formula (I), in which one of the radicals $R^1$ and $R^2=(CH_2)_o$—$CH_3$ where o=X-4 and the remaining radical $R^1$ or $R^2=(CH_2)_o$—$CH_3$ where o=Y-4.

"monoRL-CXCY" is understood to mean mono-rhamnolipids of the general formula (I), in which one of the radicals $R^1$ and $R^2=(CH_2)_o$—$CH_3$ where o=X-4 and the remaining radical $R^1$ or $R^2=(CH_2)_o$—$CH_3$ where o=Y-4.

The nomenclature used therefore does not differ between "CXCY" and "CYCX".

For rhamnolipids where m=0, monoRL-CX or diRL-CX is used accordingly.

If one of the abovementioned indices X and/or Y is provided with ":Z", this signifies that the respective radical $R^1$ and/or $R^2$=an unbranched, unsubstituted hydrocarbon radical having X-3 or Y-3 carbon atoms having Z double bonds.

To determine the content of rhamnolipids in the context of the present invention, only the mass of the rhamnolipid anion is considered, i.e. "general formula (I) less one hydrogen".

To determine the content of rhamnolipids in the context of the present invention, all rhamnolipids are converted by acidification into the protonated form (cf. general formula (I)) and quantified by HPLC.

It is preferred according to the instant invention that the compositions comprise 51% by weight to 95% by weight, preferably 70% by weight to 90% by weight, particularly preferably 75% by weight to 85% by weight, of diRL-C10C10, where the percentages by weight refer to the sum total of all rhamnolipids present.

It is preferred according to the instant invention that the compositions comprise 0.5% by weight to 9% by weight, preferably 0.5% by weight to 3% by weight, particularly preferably 0.5% by weight to 2% by weight, of monoRL-C10C10, where the percentages by weight refer to the sum total of all rhamnolipids present.

Preferred compositions according to the instant invention are characterized in that the weight ratio of all di-rhamnolipids present to all mono-rhamnolipids present is greater than 51:49, particularly greater than 91:9, preferably greater than 97:3, particularly preferably greater than 98:2.

It is preferred according to the instant invention that the compositions comprise 0.5 to 25% by weight, preferably 5% by weight to 15% by weight, particularly preferably 7% by weight to 12% by weight, of diRL-C10C12, where the percentages by weight refer to the sum total of all rhamnolipids present.

It is preferred according to the instant invention that the compositions comprise 0.1% by weight to 5% by weight, preferably 0.5% by weight to 3% by weight, particularly preferably 0.5% by weight to 2% by weight, of monoRL-C10C12 and/or, preferably and, 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

Particularly preferred compositions according to the instant invention are characterized in that they comprise
  0.5% by weight to 15% by weight, preferably 3% by weight to 12% by weight, particularly preferably 5% by weight to 10% by weight, of diRL-C10C12:1,
  0.5 to 25% by weight, preferably 5% by weight to 15% by weight, particularly preferably 7% by weight to 12% by weight, of diRL-C10C12,
  0.1% by weight to 5% by weight, preferably 0.5% by weight to 3% by weight, particularly preferably 0.5% by weight to 2% by weight, of monoRL-C10C12 and
  0.1% by weight to 5% by weight, preferably 0.5% by weight to 3% by weight, particularly preferably 0.5% by weight to 2% by weight, of monoRL-C10C12:1,
  where the percentages by weight refer to the sum total of all rhamnolipids present.

In connection with the present invention, the term "glucolipid" is understood as meaning compounds of the general formula (II) or salts thereof, formula (II)

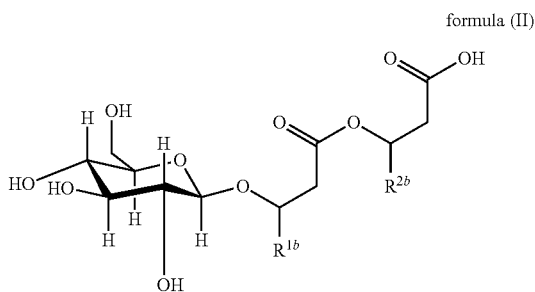

where
R$^{1b}$ and R$^{2b}$=independently of one another identical or different organic radical having 2 to 24 carbon atoms, in particular optionally branched, optionally substituted, in particular hydroxy-substituted, optionally unsaturated, in particular optionally mono-, di- or tri-unsaturated, alkyl radical, preferably one selected from the group consisting of pentenyl, heptenyl, nonenyl, undecenyl and tridecenyl and (CH$_2$)$_p$—CH$_3$ where p=1 to 23, preferably 4 to 12.

Distinct glucolipids are abbreviated according to the following nomenclature:

"GL-CXCY" is understood as meaning glucolipids of the general formula (II) in which one of the radicals R$^{1b}$ and R$^{2b}$=(CH$_2$)$_p$—CH$_3$ where p=X-4 and the remaining radical R$^{1b}$ or R$^{2b}$=(CH$_2$)$_p$—CH$_3$ where p=Y-4.

The nomenclature used thus does not differentiate between "CXCY" and "CYCX".

If one of the aforementioned indices X and/or Y is provided with ":Z", then this means that the respective radical R$^{1b}$ and/or R$^{2b}$=an unbranched, unsubstituted hydrocarbon radical with X-3 or Y-3 carbon atoms having Z double bonds.

To determine the content of glucolipids in the context of the present invention, only the mass of the glucolipid anion is considered, i.e. "general formula (I) less one hydrogen".

To determine the content of glucolipids in the context of the present invention, all glucolipids are converted by acidification into the protonated form (cf. general formula (II)) and quantified by HPLC.

Preferred compositions according to the instant invention comprise glucolipids of general formula (II), characterized in that the composition comprises at least 51% by weight to preferably 98% by weight, preferably 60% by weight to 95% by weight, more preferably 70% by weight to 90% by weight, particularly preferably 75% by weight to 85% by weight, glucolipids GL-C10C10 of the general formula (II) with R$^{1b}$ and R$^{2b}$=(CH$_2$)$_6$—CH$_3$, where the percentages by weight refer to the sum of all of the glucolipids of the general formula (II) present.

It may be advantageous and is therefore preferred if the mixture composition according to the instant invention comprises 1% by weight to 30% by weight, preferably 5% by weight to 25% by weight, particularly preferably 10% by weight to 20% by weight, of GL-C8C10, where the percentages by weight refer to the sum of all of the glucolipids of the general formula (II) present.

A preferred composition according to the instant invention is characterized in that the composition comprises 0.5% by weight to 20% by weight, preferably 3% by weight to 17% by weight, particularly preferably 5% by weight to 15% by weight, of GL-C10C12:1, where the percentages by weight refer to the sum of all of the glucolipids of the general formula (II) present.

A further preferred composition according to the instant invention is characterized in that the composition comprises 0.5% by weight to 20% by weight, preferably 2% by weight to 15% by weight, particularly preferably 3% by weight to 12% by weight, of GL-C10C12 where the percentages by weight refer to the sum of all of the glucolipids of the general formula (II) present.

A particularly preferred composition according to the instant invention is characterized in that the composition comprises 1% by weight to 30% by weight, preferably 5% by weight to 25% by weight, particularly preferably 10% by weight to 20% by weight, of GL-C8C10, 0.5% by weight to 20% by weight, preferably 3% by weight to 17% by weight, particularly preferably 5% by weight to 15% by weight, of GL-C10C12:1, 0.5% by weight to 20% by weight, preferably 2% by weight to 15% by weight, particularly preferably 3% by weight to 12% by weight, of GL-C10C12 where the percentages by weight refer to the sum of all of the glucolipids of the general formula (II) present.

A very particularly preferred composition according to the instant invention is characterized in that the composition comprises 10% by weight to 20% by weight, of GL-C8C10,
5% by weight to 15% by weight, of GL-C10C12:1,
3% by weight to 12% by weight, of GL-C10C12
where the percentages by weight refer to the sum of all of the glucolipids of the general formula (II) present.

Sophorolipids may be used in accordance with the instant invention in their acid form or their lactone form. With regard to the term "acid form" of sophorolipids reference is made to the general formula (Ia) of EP2501813, and with regard to the term "lactone form" of sophorolipids reference is made to the general formula (Ib) of EP2501813.

To determine the content of sophorolipids in the acid or lactone form in a composition, refer to EP1411111B1, page 8, paragraph [0053].

Preferred compositions according to the instant invention are characterized in that the pH of the composition at 25° C. is from 4.5 to 7.0, preferably from 4.8 to 6.6 and particularly preferably from 5.2 to 6.0.

A preferred composition according to the instant invention is characterized in that it comprises 40% by weight to 70% by weight, preferably 45% by weight to 55% by weight of at least one glycolipid, where the percentages by weight refer to the total composition.

These concentrated compositions according to the instant invention have the advantage, that their stability during storage at low temperatures is improved. These concentrated compositions according to the instant invention show an improved odor. These concentrated compositions according to the instant invention show an improved processability. Furthermore, the concentrated compositions according to the instant invention have an improved color-stability over longer storage times.

A preferred composition according to the instant invention is characterized in that it comprises 0.2% by weight to 12% by weight, preferably 0.4% by weight to 8% by weight of at least one glycolipid, where the percentages by weight refer to the total composition.

These diluted compositions according to the instant invention have the advantage, that the foam creaminess is improved. These diluted compositions according to the instant invention show an improved skin compatibility.

A preferred composition according to the instant invention is characterized in that said composition comprises at least one preservative selected from the group consisting of p-anisic acid, levulinic acid, lactic acid and citric acid, preferably p-anisic acid, and salts of the aforementioned acids, preferably at a concentration of from 0.01% by weight to 14% by weight, preferably from 0.02% by weight to 11%, by weight, where the percentages by weight refer to the total composition.

Addition of these preservatives to compositions according to the instant invention has the advantage, that the solubilizing performance towards cosmetic oils is improved. Addition of these preservatives to compositions according to the instant invention leads to an improved taste. This finding makes them suitable for any oral care application.

The present invention further provides a method for preparing a formulation, preferably a cosmetical or pharmaceutical formulation, of glycolipids comprising the steps of
a) providing a composition comprising
  40% by weight to 70% by weight, preferably 45% by weight to 55% by weight of at least one glycolipid,
  1.0% by weight to 14% by weight, preferably 2.0% by weight to 11% by weight, triethyl citrate, and
  water,
  where the percentages by weight refer to the total composition, characterized in that the weight ratio of all glycolipids to all triethyl citrate comprised in the composition is in the range of 5:1 to 20:1, preferably from 6:1 to 15:1, particular preferably from 7:1 to 12:1.
b) diluting the composition with at least partially water to a formulation comprising 0.2% by weight to 20% by weight, preferably 0.4% by weight to 15% by weight of the at least one glycolipid, where the percentages by weight refer to the total formulation.

In preferred methods of the instant invention preferred glycolipids of the composition according to the instant invention are used.

A preferred method according to the instant invention is characterized in that the pH of the formulation in method step b) is adjusted to a pH of at 25° C. from 4.5 to 7.0, preferably from 4.8 to 6.6 and particularly preferably from 5.2 to 6.0.

A method preferred according to the instant invention is characterized in that the pH is adjusted in method step b) by adding an organic or inorganic base, preferably in concentrated form.

The term "base in concentrated form" in the context of the present invention is understood to mean that the base is added in the form of a composition comprising at least 60% by weight, in particular at least 80% by weight of base, where the percentages by weight refer to the total composition added.

In the method according to the instant invention, preference is given to using bases selected from the group comprising, preferably consisting of, alkali metal and alkaline earth metal hydroxides such as NaOH, KOH, Mg(OH)$_2$, Ca(OH)$_2$, Al(OH)$_3$, NH$_4$OH, primary amines, secondary amines, tertiary amines and quaternary amines.

Exemplary representatives of suitable amines are 2-aminoethanol (also ethanolamine, MEA), diethanolamine (also DEA), 2,2',2"-nitrilotriethanol (also triethanolamine, TEA), 1-aminopropan-2-ol (also monoisopropanolamine), [(2-hydroxyethyl)trimethylammonium] (also choline) ethylenediamine, diethylenetriamine, triethylenetetramine, tetraethylenepentamine, 1,4-diethylenediamine (also piperazine), aminoethylpiperazine, aminoethylethanolamine, tetramethylammonium hydroxide, tetraethylammonium hydroxide, tetrapropylammonium hydroxide, tetrabutylammonium hydroxide, wherein preference is given to using 2-aminoethanol (also ethanolamine, MEA), diethanolamine (also DEA), 2,2',2"-nitrilotriethanol (also triethanolamine, TEA), 1-aminopropan-2-ol (also monoisopropanolamine) and (2-hydroxyethyl)trimethylammonium (also choline).

Particularly preferred bases are NaOH, KOH, NH$_3$, NH$_4$OH and triethanolamine.

It is also possible to use mixtures of the abovementioned bases in accordance with the invention.

A preferred method according to the instant invention is characterized in that it comprises method step c) adding at least one additional component selected from the group of emollients, emulsifiers, thickeners/viscosity regulators/stabilizers, UV light protection filters, antioxidants, hydrotropes or polyols, solids and fillers, film formers, pearlescence additives, deodorant and antiperspirant active ingredients, insect repellents, self-tanning agents, preservatives, conditioning agents, perfumes, dyes, odor absorbers, cosmetic active ingredients, care additives, superfatting agents and solvents. Substances which can be used as exemplary representatives of the individual groups are known to those skilled in the art and can be found for example in German application DE 102008001788.4. This patent application is hereby incorporated as reference and thus forms part of the disclosure.

As regards further optional components and the amounts used of these components, reference is made expressly to the relevant handbooks known to those skilled in the art, for example K. Schrader, "Grundlagen and Rezepturen der Kosmetika [Cosmetics-fundamentals and formulations]", 2nd edition, pages 329 to 341, Huthig Buch Verlag Heidelberg.

The amounts of the particular additives are determined by the intended use.

Typical boundary formulations for the respective applications are known prior art and are contained for example in the brochures of the manufacturers of the particular base and active ingredients.

These existing formulations can generally be adopted unchanged. However, if required, for adjustment and optimization, the desired modifications can be undertaken by simple tests without complication.

The present invention further provides the use of triethyl citrate to stabilize the foam of an aqueous composition containing at least one glycolipid, preferably selected from the group of rhamnolipids, glucolipids and sophorolipids, in particular rhamnolipids and glucolipids, in most particular rhamnolipids.

The present invention further provides the use of triethyl citrate to inverse the dependency of foam stability versus pH in an aqueous composition containing at least one glycolipid, preferably selected from the group of rhamnolipids, glucolipids and sophorolipids, in particular rhamnolipids and glucolipids, in most particular rhamnolipids.

Figure 1:
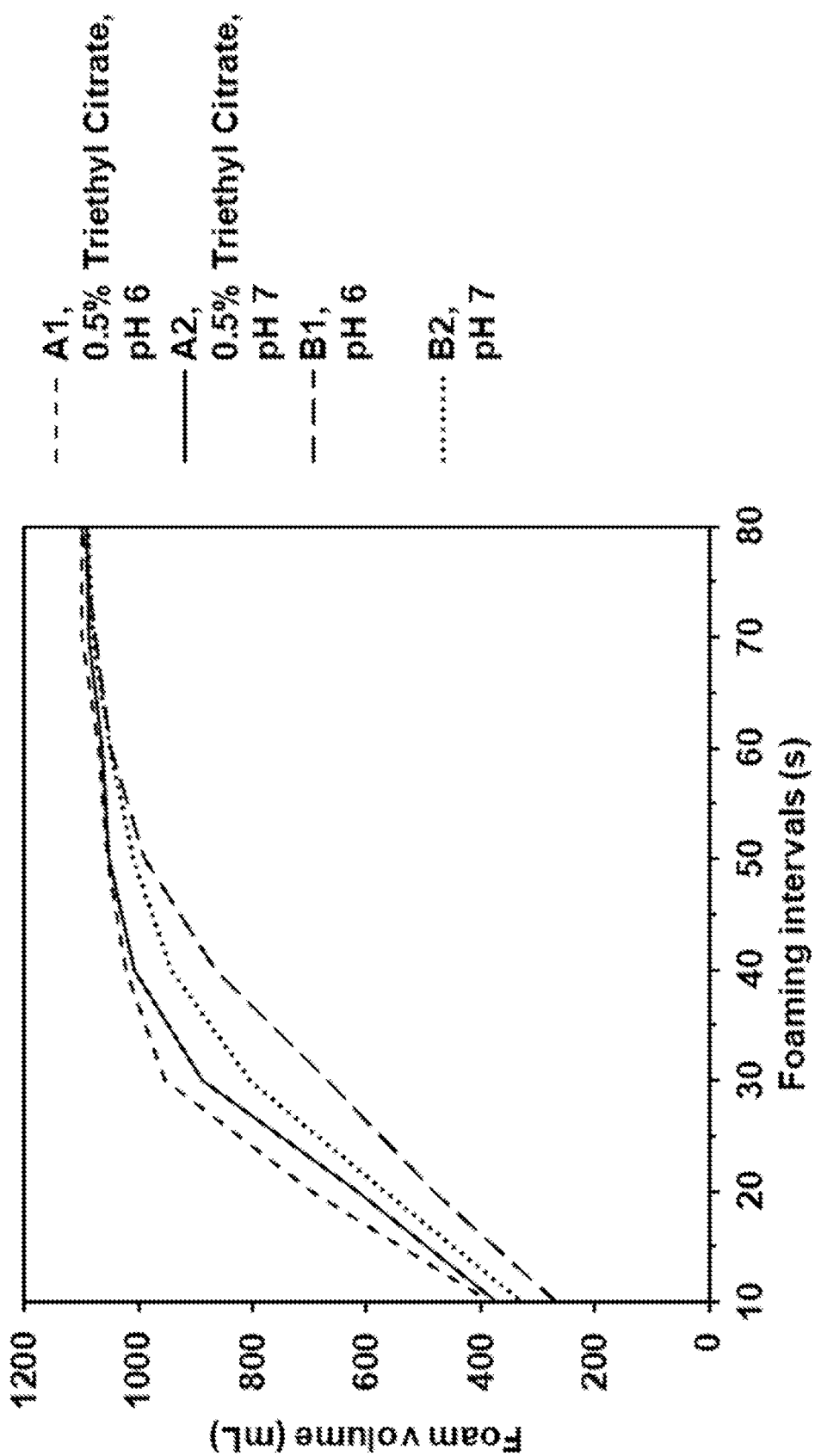
FIG. 1 illustrates the foam volume over time for different rhamnolipid containing compositions with and without triethyl citrate.

The present invention is illustratively described in the examples listed below without any intention of limiting the instant invention, whose scope is determined by the entire description, to the embodiments referred to in the examples.

EXAMPLES

List of Raw Materials Used

| INCI | Trade name, company |
| --- | --- |
| Perfume Pink Grapefruit | IFF Inc. |
| Rosemary oil | Frey & Lau GmbH |
| Glycolipid | RHEANCE ® One Evonik Nutrition & Care GmbH |
| Triethyl Citrate | dermofeel ® TEC eco |
| Cocamidopropyl Betaine | TEGO ® Betain F 50 Evonik Nutrition & Care GmbH |
| Sophorolipid | REWOFERM ® SL One, Evonik Operations GmbH |
| Glucolipid | obtained as described in. WO2019/154970 |

Example 1: Evaluation of Foaming Properties Using the SITA Foam Tester

Foamability of surfactants and surfactant-based cleansing products is an important consumer-perceived attribute. Consumers associate fast flash foaming and high foam volumes with efficacy and high quality. Both parameters can be determined using the "SITA foam tester R-2000" measuring device from SITA Messtechnik GmbH. In this device, foam is generated by introducing air into a defined volume of a surfactant solution through a special rotor. The total volume of liquid and resulting foam is measured over time by means of a computer-controlled sensing technique. Using this method, composition example A containing rhamnolipid and triethyl citrate was evaluated for its foamability in comparison to a composition example containing rhamnolipid. Composition A (according to the invention) was prepared as follows: 384 g of freeze-dried, unpreserved Rhamnolipid were dissolved in 374 g of water. The mixture was heated to 50° C. while stirring and 40 g triethyl citrate (Dermofeel® TEC eco) were added. Stirring for further 30 min and cooling down to room temperature finally provided a crystal-clear solution of composition A.

For the preparation of composition B (not according to the invention), 96 g of freeze-dried, unpreserved rhamnolipid were dissolved in 102 g water. Stirring for further 30 min provided a crystal-clear solution of composition B.

Using the identical method, composition example C containing sophorolipid and triethyl citrate was evaluated for its foamability in comparison to a composition example containing sophorolipid. To 95 g of an aqueous solution of sophorolipids (40%) 5 g triethyl citrate were added. After stirring for 30 min and cooling down to room temperature a crystal-clear solution of composition C was obtained. For the preparation of composition D 95 g of an aqueous solution of sophorolipids (40%) were diluted by adding 5 g of water.

Glucolipids were obtained as described in WO2019/154970. 5 g triethyl citrate were added to 95 g of an aqueous solution of glucolipids (50%). After stirring for 30 min and cooling down to room temperature finally provided a crystal-clear solution of composition E. For the preparation of composition F 95 g of an aqueous solution of glucolipids (50%) were diluted by adding 5 g of water.

For evaluating the foaming performance, compositions A and B were each diluted to a concentration of 0.5 wt % active surfactant matter with water of a total hardness of 10° dH (German hardness). The dilutions of compositions A and B were then split into two sub-batches of 600 ml each and the pH values of these sub-batches were adjusted to pH 6.0 (A1, B1) and pH 7.0 (A2, B2) using a 25 wt % aqueous solution of sodium hydroxide. 300 ml of each test solution were tested for their foamability at 30° C. using a constant stirring speed of 1500 rpm for 10 sec. A total of 8 such measurement intervals was carried out for each test solution. All samples were tested in duplicate. FIG. 1 illustrates the foam volume over time for each test solution.

Measurement parameters: temperature: 30° C.±0.5° C.; sample volume/measurement: 300 ml; concentration of test sample: 0.5 wt % in water (10° dH (=german hardness)), pH adjusted with NaOH, stirring speed: 1500 rpm; stirring time: 10 sec; number of intervals: 8; number of replications: 2

As seen in FIG. 1, the composition according to the invention (A) shows a better overall performance in the SITA foam test compared to composition B, represented by faster flash foaming and higher foam volume. Surprisingly, the pH dependency reverses in case of the composition according to the invention (A): while composition B achieves best flash foaming and higher foam volumes at pH 7.0 and decreasing performance with decreasing pH, the foaming characteristics of the composition according to the invention (A) improve when decreasing the pH from 7.0 to 6.0. As cosmetic formulations are usually adjusted to pH values <7.0 for a better skin compatibility, excellent foaming at pH<7.0 is a desired feature for cosmetic cleansing ingredients and formulations.

Figure 2:
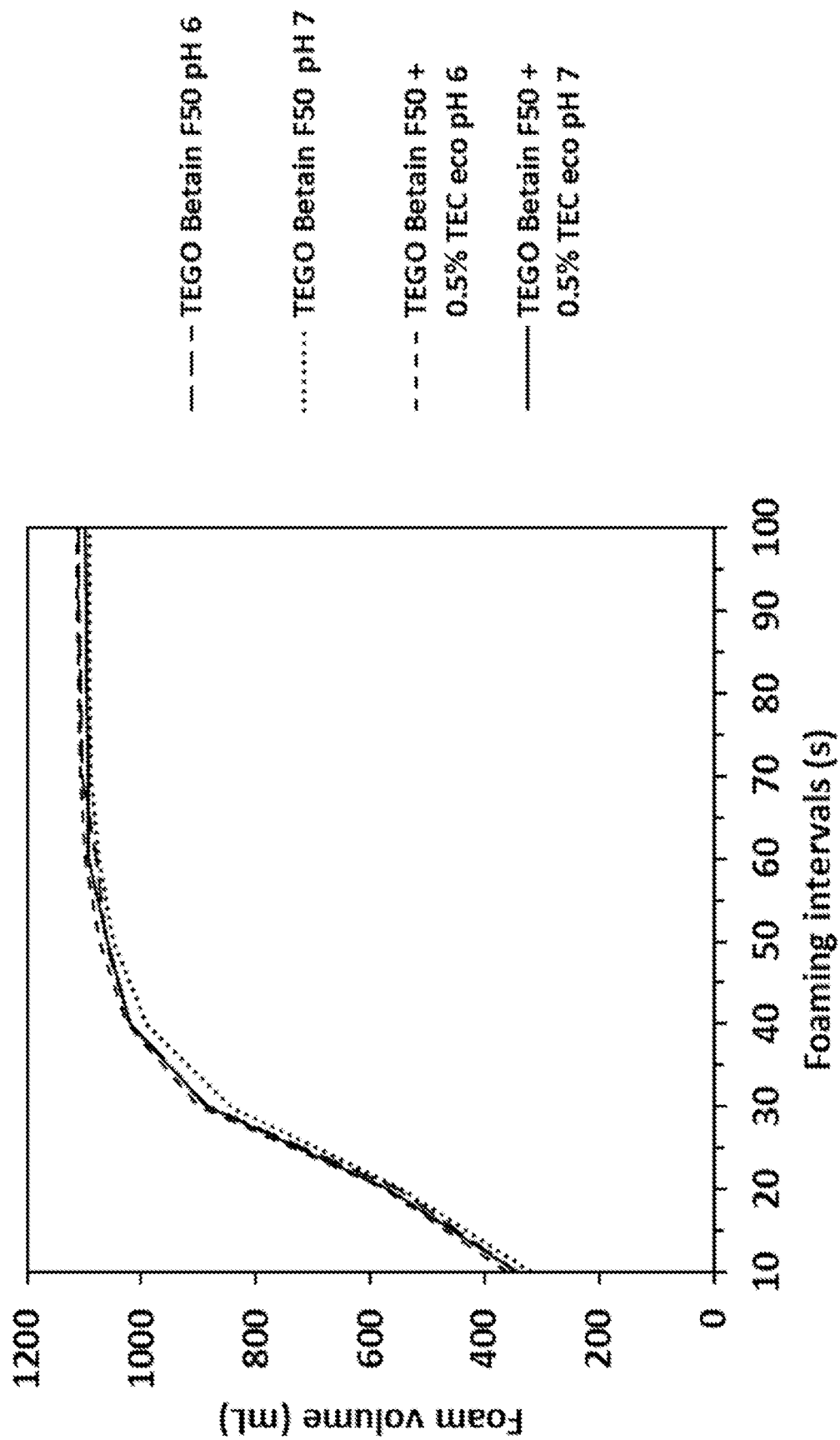
FIG. 2 illustrates the foam volume over time for different betaine containing compositions with and without triethyl citrate.

The results shown in FIG. 2 are from the same protocol, which was repeated by using cocamidopropyl betaine instead of rhamnolipids. Here, independent of pH, no differences in the foaming performance were observed.

For evaluating the foaming performance, compositions C, D, E and F were each diluted to a concentration of 0.5 wt % active surfactant matter with water of a total hardness of 10° dH (German hardness). For the dilutions of compositions C, D the pH values of these sub-batches were adjusted to pH 6.0 (C1, D1) 25 wt % aqueous solution of sodium hydroxide and citric acid. 300 ml of each test solution were tested for their foamability at 30° C. using a constant stirring speed of 1500 rpm for 10 sec. A total of 8 such measurement intervals was carried out for each test solution. All samples were tested in duplicate.

For the dilutions of compositions E, F the pH values of these sub-batches were adjusted to pH 5.0 (E1, F1) 25 wt % aqueous solution of sodium hydroxide and citric acid. 300 ml of each test solution were tested for their foamability at 30° C. using a constant stirring speed of 1500 rpm for 10 sec. A total of 8 such measurement intervals was carried out for each test solution. All samples were tested in duplicate.

Figure 4:
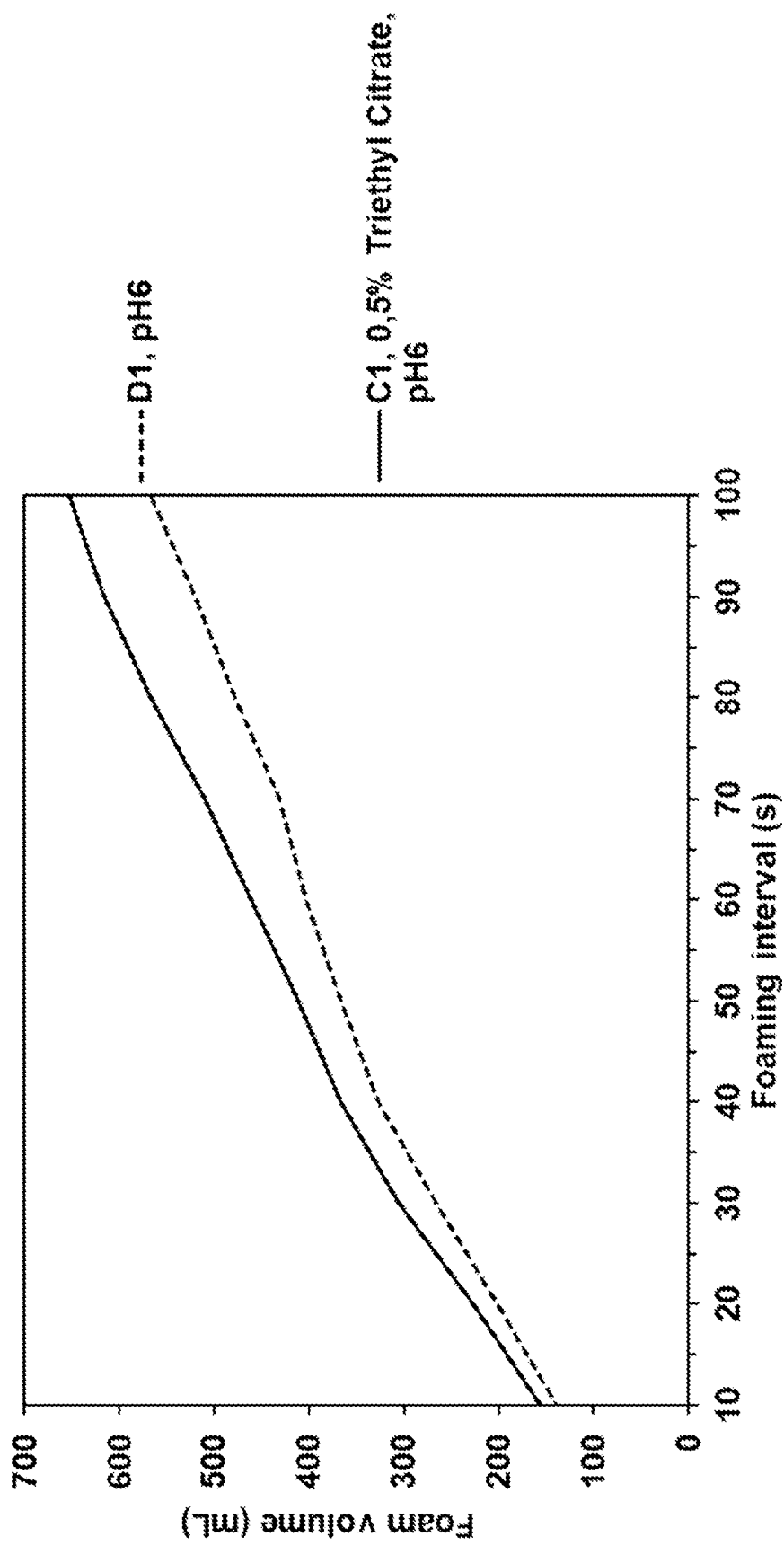
FIG. 4 illustrates the foam volume over time for sophorolipid containing compositions with and without triethyl citrate.

As seen in FIG. 4, the composition according to the invention (C) shows a better overall performance in the SITA foam test compared to composition D, represented by faster flash foaming and higher foam volume.

Figure 5:
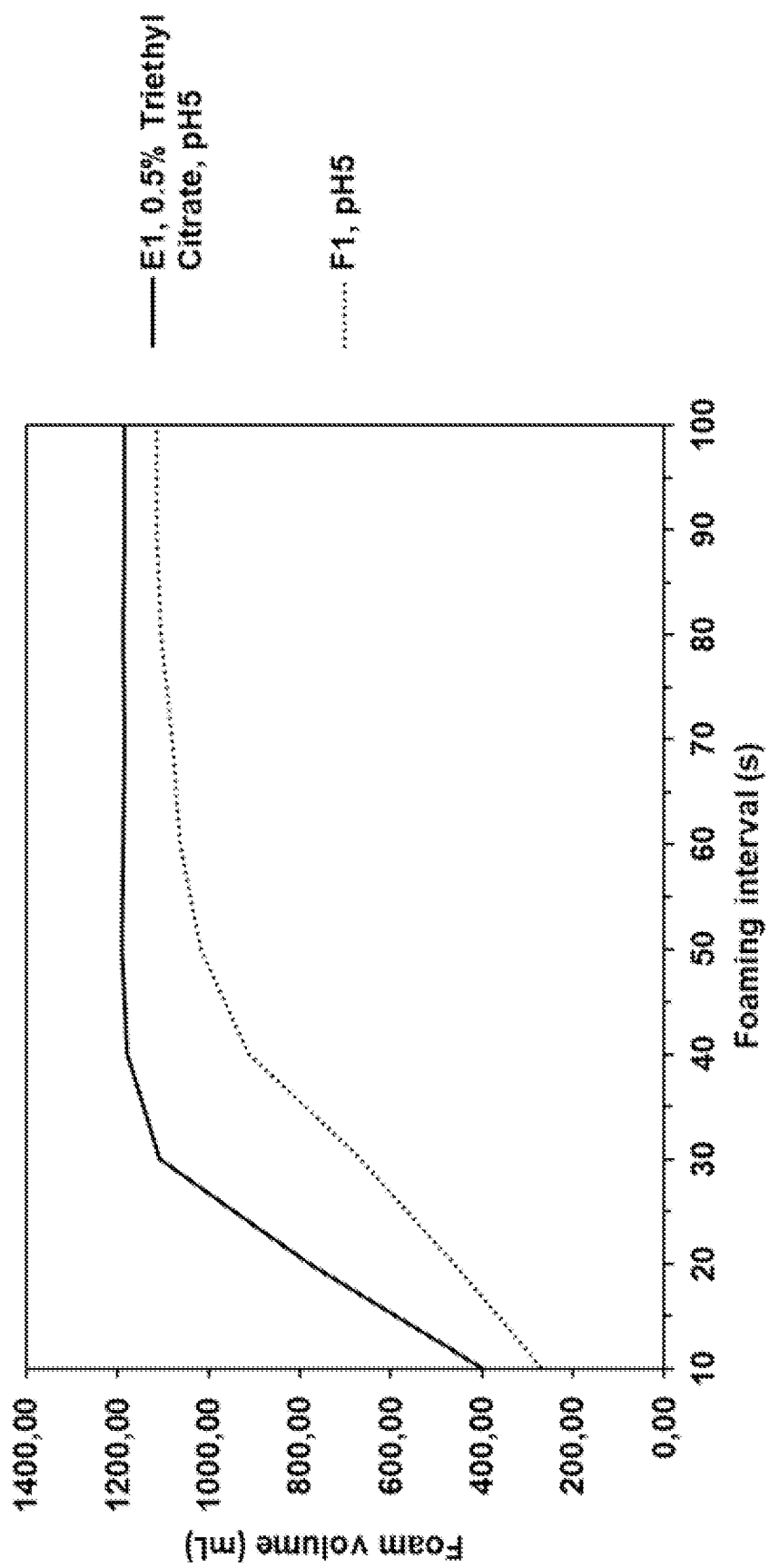
FIG. 5 illustrates the foam volume over time for glucolipid containing compositions with and without triethyl citrate.

As seen in FIG. 5, the composition according to the invention (E) shows a better overall performance in the SITA foam test compared to composition F, represented by faster flash foaming and higher foam volume.

Example 2: Solubilization of Essential Oils

Figure 3:
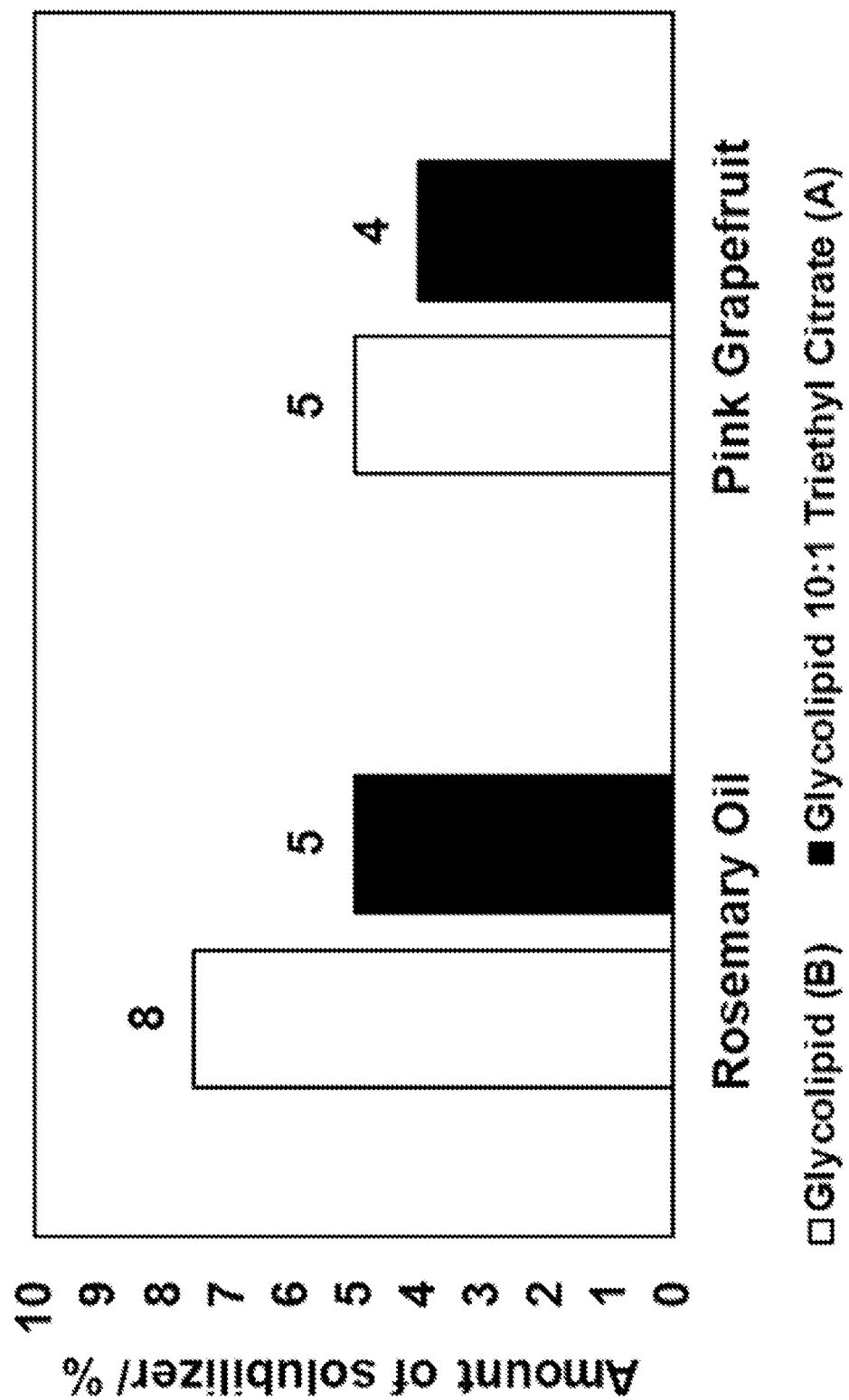
FIG. 3 illustrates the solubilization of different essential oils by rhamnolipids with and without the presence of triethyl citrate

The dissolving power was investigated by mixing the essential oil with a rhamnolipid or a mixture of rhamnolipid and triethyl citrate followed by dilution with water. The minimum required amount of solubilizer used to give a clear aqueous solution from 1% of the oil was determined. A test was designed by mixing a defined amount of solubilizer (1 g-20 g) and 1 g of the oil. The sample was visually judged, stored for 24 h and judged again. In FIG. 3 the results are listed.

In case of the composition according to the invention (A), a mixture of rhamnolipid (10 parts) and tritethyl citrate (1 part), a lower amount of solubilizer is needed to solubilize rosemary oil and Pink Grapefruit perfume as compared to the non-inventive composition (B), pure rhamnolipid.

The invention claimed is:

1. A composition, comprising:
   0.2% by weight to 70% by weight of at least one glycolipid,
   0.01% by weight to 14% by weight of triethyl citrate, and water,
   wherein the percentages by weight refer to the total composition, wherein a weight ratio of all glycolipids to all triethyl citrate comprised in the composition is in a range of from 5:1 to 20:1.

2. The composition according to claim 1, wherein a pH of the composition at 25° C. is from 4.5 to 7.0.

3. The composition according to claim 1,
   wherein the composition comprises 40% by weight to 70% by weight of the at least one glycolipid, wherein the percentages by weight refer to the total composition.

4. The composition according to claim 1,
   wherein the composition comprises 0.2% by weight to 12%, by weight of the at least one glycolipid, wherein the percentages by weight refer to the total composition.

5. The composition according to claim 1, wherein said composition comprises 51% by weight to 95% by weight of diRL-C10C10,
   wherein the percentages by weight refer to a sum total of all rhamnolipids present,
   wherein diRL-C10C10 is a di-rhamnolipid of formula (I) or salts thereof, in which radicals $R^1$ and $R^2$=$(CH_2)_o$—$CH_3$ wherein o=6,
   wherein formula (I) is

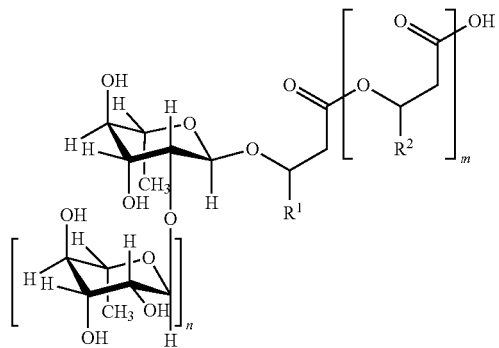

wherein
m=1,
n=1.

6. The composition according to claim 1, wherein said composition comprises 0.5% by weight to 9% by weight of monoRL-C10C10, wherein the percentages by weight refer to a sum total of all rhamnolipids present,
   monoRL-C10C10 is a mono-rhamnolipid of formula (I) in which radicals $R^1$ and $R^2$=$(CH_2)_o$—$CH_3$ wherein o=6,
   wherein formula (I) is

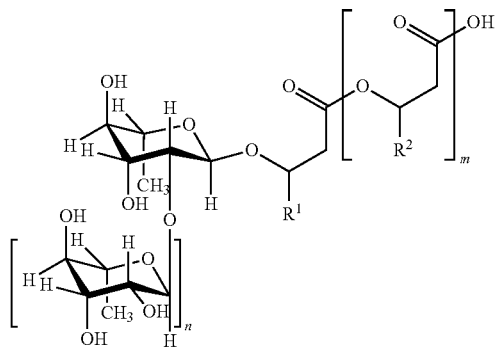

wherein
m=1,
n=0.

7. The composition according to claim 1, which comprises di-rhamnolipids and mono-rhamnolipids,
   wherein a weight ratio of all di-rhamnolipids present to all mono-rhamnolipids present is greater than 51:49.

8. The composition according to claim 1, wherein said composition comprises 0.5 to 25% by weight of diRL-C10C12, wherein the percentages by weight refer to a sum total of all rhamnolipids present,
   wherein diRL-C10C12 is a di-rhamnolipid of formula (I) and salts thereof, in which one of radicals $R^1$ and $R^2$=$(CH_2)_o$—$CH_3$ wherein o=6 and remaining radical $R^1$ or $R^2$=$(CH_2)_o$—$CH_3$ wherein o=8,
   wherein formula (I) is

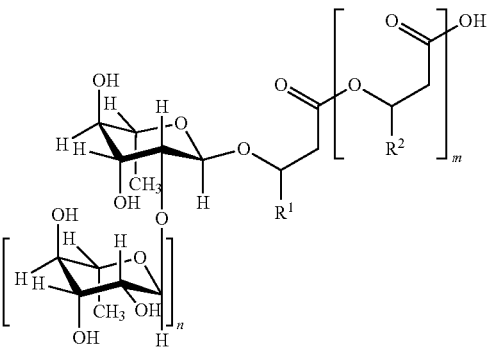

wherein
m=1,
n=1.

9. The composition according to claim 1, wherein said composition comprises:
   0.1% by weight to 5% by weight of monoRL-C10C12, and/or
   0.1% by weight to 5% by weight of monoRL-C10C12:1, wherein the percentages by weight refer to a sum total of all rhamnolipids present, wherein monoRL-C10C12 is a mono-rhamnolipid of formula (I), in which one of radicals $R^1$ and $R^2$=$(CH_2)_o$—$CH_3$ wherein o=6 and remaining radical $R^1$ or $R^2$=$(CH_2)_o$—$CH_3$ wherein o=8, wherein monoRL-C10C12:1 is a mono-rhamnolipid of formula (I), in which one of radicals $R^1$ and $R^2$=$(CH_2)_o$—$CH_3$ where o=6 and remaining radical $R^1$ or $R^2$=an unbranched, unsubstituted hydrocarbon radical having 9 carbon atoms having 1 double bond, wherein formula (I) is

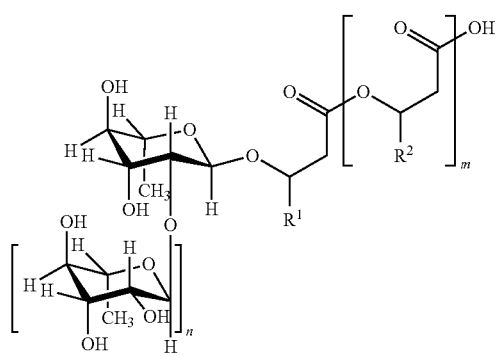

wherein m=1, n=0.

10. The composition according to claim 1, wherein said composition comprises:

0.5% by weight to 15% by weight of diRL-C10C12:1, 0.5 to 25% by weight of diRL-C10C12, 0.1% by weight to 5% by weight of monoRL-C10C12, and 0.1% by weight to 5% by weight of monoRL-C10C12:1, wherein the percentages by weight refer to a sum total of all rhamnolipids present, wherein diRL-C10C12:1 is a di-rhamnolipid of formula (I), in which n=1 and one of radicals $R^1$ and $R^2$=$(CH_2)_o$—$CH_3$ wherein o=6 and remaining radical $R^1$ or $R^2$=an unbranched, unsubstituted hydrocarbon radical having 9 carbon atoms having 1 double bond, wherein diRL-C10C12 is a di-rhamnolipid of formula (I) and salts thereof, in which n=1 and one of radicals $R^1$ and $R^2$=$(CH_2)_o$—$CH_3$ wherein o=6 and remaining radical $R^1$ or $R^2$=$(CH_2)_o$—$CH_3$ wherein o=8, wherein monoRL-C10C12 is a mono-rhamnolipid of formula (I), in which n=0 and one of radicals $R^1$ and $R^2$=$(CH_2)_o$—$CH_3$ wherein o=6 and remaining radical $R^1$ or $R^2$=$(CH_2)_o$—$CH_3$ wherein o=8, wherein monoRL-C10C12:1 is a mono-rhamnolipid of formula (I), in which n=0 and one of radicals $R^1$ and $R^2$=$(CH_2)_o$—$CH_3$ where o=6 and remaining radical $R^1$ or $R^2$=an unbranched, unsubstituted hydrocarbon radical having 9 carbon atoms having 1 double bond, wherein formula (I) is

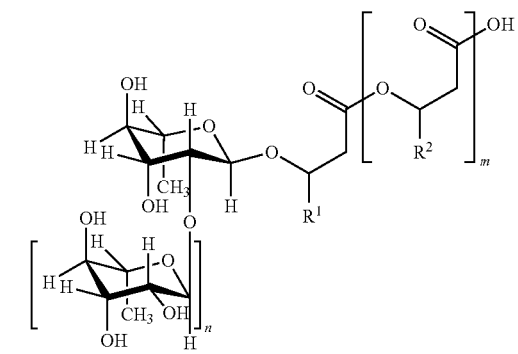

wherein m=1.

11. The composition according to claim 1, wherein said composition comprises at least one preservative selected from the group consisting of p-anisic acid, levulinic acid, lactic acid, citric acid, and a salt of the aforementioned acids.

12. A method for preparing a formulation of at least one glycolipid, the method comprising:

a) providing a composition comprising

40% by weight to 70% by weight of at least one glycolipid, 2.0% by weight to 14% by weight of triethyl citrate, and water, wherein the percentages by weight refer to the total composition, wherein a weight ratio of all glycolipids to all triethyl citrate comprised in the composition is in a range of from 5:1 to 20:1, and b) diluting the composition with at least partially water to a formulation comprising 0.2% by weight to 12% by weight of the at least one glycolipid, where the percentages by weight refer to the total formulation.

13. The method according to claim 12, wherein a pH of the formulation in b) is adjusted to a pH of at 25° C. from 4.5 to 7.0.

14. A method, comprising:

adding triethyl citrate to an aqueous composition containing at least one glycolipid, to stabilize a foam of the aqueous composition, thereby obtaining a stabilized foam of the aqueous composition which comprises 0.2% by weight to 70% by weight of said at least one glycolipid, 0.01% by weight to 14% by weight of said triethyl citrate, and water, wherein the percentages by weight refer to the total stabilized foam, wherein a weight ratio of all glycolipids to all triethyl citrate comprised in the stabilized foam is in a range of from 5:1 to 20:1.

15. The composition according to claim 1, comprising:

0.4% by weight to 55% by weight of the at least one glycolipid, and 0.02% by weight to 11% by weight of triethyl citrate, wherein the percentages by weight refer to the total composition.

16. The composition according to claim 9, wherein the composition comprises:

0.1% by weight to 5% by weight of the monoRL-C10C12, and 0.1% by weight to 5% by weight of the monoRL-C10C12:1, wherein the percentages by weight refer to the sum total of all rhamnolipids present, wherein monoRL-C10C12 is a mono-rhamnolipid of formula (I), in which n=0 and one of radicals $R^1$ and $R^2$=(CH$_2$)$_o$—CH$_3$ wherein o=6 and remaining radical $R^1$ or $R^2$=an (CH$_2$)$_o$—CH$_3$ wherein o=8, wherein monoRL-C10C12:1 is a mono-rhamnolipid of formula (I), in which n=0 and one of radicals $R^1$ and $R^2$=(CH$_2$)$_o$—CH$_3$ where o=6 and remaining radical $R^1$ or $R^2$=an unbranched, unsubstituted hydrocarbon radical having 9 carbon atoms having 1 double bond, wherein formula (I) is

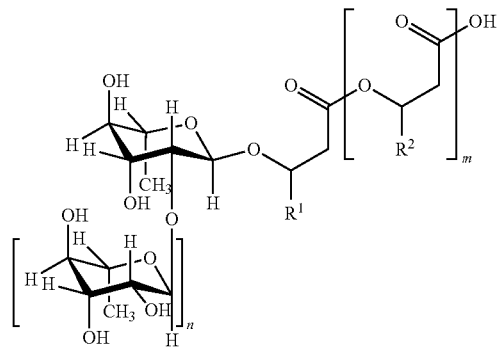

wherein
m=1.

17. The composition according to claim 11, wherein the composition comprises the at least one preservative at a concentration of from 0.01% by weight to 14% by weight, where the percentages by weight refer to the total composition.

18. The method according to claim 12, wherein the formulation is a cosmetical or pharmaceutical composition.

19. The method according to claim 13, wherein the pH of the formulation is adjusted in b) by adding an organic or inorganic base.

* * * * *